United States Patent
Oh et al.

(10) Patent No.: US 9,526,842 B2
(45) Date of Patent: Dec. 27, 2016

(54) APPARATUS AND METHOD FOR MEASURING DOSE IN INJECTOR

(75) Inventors: Jung-Taek Oh, Seoul (KR); Sun-Tae Jung, Gyeonggi-do (KR)

(73) Assignee: Samsung Electronics Co., Ltd (KR)

( * ) Notice: Subject to any disclaimer, the term of this patent is extended or adjusted under 35 U.S.C. 154(b) by 766 days.

(21) Appl. No.: 13/187,793

(22) Filed: Jul. 21, 2011

(65) Prior Publication Data
US 2012/0022458 A1    Jan. 26, 2012

(30) Foreign Application Priority Data

Jul. 21, 2010    (KR) .................. 10-2010-0070547

(51) Int. Cl.
| | | |
|---|---|---|
| *A61M 5/315* | (2006.01) | |
| *A61M 5/31* | (2006.01) | |
| *G01D 5/14* | (2006.01) | |
| *G01D 5/245* | (2006.01) | |
| *G01D 5/347* | (2006.01) | |

(52) U.S. Cl.
CPC ..... *A61M 5/31551* (2013.01); *A61M 5/31525* (2013.01); *A61M 2005/3125* (2013.01); *A61M 2005/3126* (2013.01); *A61M 2205/3306* (2013.01); *A61M 2205/3317* (2013.01); *G01D 5/145* (2013.01); *G01D 5/2451* (2013.01); *G01D 5/3473* (2013.01)

(58) Field of Classification Search
CPC .............. A61M 5/31551; A61M 5/31525; A61M 2005/3126; A61M 2005/3125; A61M 2205/3317; A61M 2205/3306; A61M 5/31556; A61M 5/31558; A61M 5/31566; A61M 5/31573; A61M 5/31535; A61M 5/31533; G01D 5/3473; G01D 5/145; G01D 5/2451
USPC ................. 604/189, 207–211, 187, 181, 218
See application file for complete search history.

(56) References Cited

U.S. PATENT DOCUMENTS

| | | | | |
|---|---|---|---|---|
| 5,593,390 | A | * | 1/1997 | Castellano et al. ........... 604/187 |
| 6,068,615 | A | | 5/2000 | Brown et al. |
| 6,110,148 | A | | 8/2000 | Brown et al. |
| 7,316,670 | B2 | * | 1/2008 | Graf et al. .................... 604/207 |

(Continued)

FOREIGN PATENT DOCUMENTS

| | | |
|---|---|---|
| KR | 1020040019910 | 3/2004 |
| KR | 1020070028818 | 3/2007 |

(Continued)

OTHER PUBLICATIONS

Korean Office Action dated Aug. 10, 2016 issued in counterpart application No. 10-2010-0070547, 12 pages.

*Primary Examiner* — Manuel Mendez
(74) *Attorney, Agent, or Firm* — The Farrell Law Firm, P.C.

(57) ABSTRACT

Provided is an apparatus and method for measuring a dose in an injector, which is capable of measuring a dose without modifying the mechanical structure of the injector. A number sleeve is provided to pass through an injector body and is connected to be spirally movable, and a pattern for dose measurement is formed on an outer periphery of the number sleeve. The injector body includes a sensor for sensing the pattern formed on the number sleeve when the number sleeve performs a spiral movement, and a controller for measuring a dose according to a spiral movement distance of the number sleeve through the sensor.

17 Claims, 8 Drawing Sheets

(56) References Cited

U.S. PATENT DOCUMENTS

| | | |
|---|---|---|
| 7,713,229 B2 | 5/2010 | Veit et al. |
| 9,125,991 B2 * | 9/2015 | Schabbach ......... A61B 5/14532 |
| 2011/0270214 A1 * | 11/2011 | Jorgensen et al. ............ 604/500 |

FOREIGN PATENT DOCUMENTS

| | | |
|---|---|---|
| WO | WO 02/11795 | 2/2002 |
| WO | WO 02/064196 | 8/2002 |
| WO | WO 2007/099093 | 9/2007 |
| WO | WO 2007/122253 | 11/2007 |
| WO | WO 2008040477 | 4/2008 |
| WO | WO 2010/052275 | 5/2010 |

* cited by examiner

APPARATUS AND METHOD FOR MEASURING DOSE IN INJECTOR

PRIORITY

This application claims priority under 35 U.S.C. §119(a) to a Korean Patent Application filed in the Korean Intellectual Property Office on Jul. 21, 2010 and assigned Serial No. 10-2010-0070547, the contents of which are incorporated herein by reference.

BACKGROUND OF THE INVENTION

1. Field of the Invention

The present invention relates generally to an apparatus and method for measuring a dose in an injector, and more particularly, to an apparatus and method for measuring a dose in an injector, which is capable of measuring a dose without modifying the mechanical structure of the injector.

2. Description of the Related Art

A type 1 diabetic patient's body does not produce enough insulin that is essential to survival, so he or she needs to continuously measure a blood glucose level and inject an appropriate dose of insulin. Currently, an insulin pen that conveniently allows a user to personally inject insulin has been distributed on the markets. The insulin pen is designed to determine a specific dose by turning a dose-marked knob, and inject insulin by pressing a button disposed at the end of the insulin pen.

A patient records information about when and how much insulin is injected, and his or her medical attendant checks the recorded information to determine whether a patient's disease state is controlled, thereby increasing the effect of treatment.

However, for an insulin pen which allows an individual to adjust and inject a specific dose of insulin personally according to an aperiodically checked glucose level, as well as a complicated system like an insulin pump which measures a glucose level for twenty-four hours in real time and continuously injects a slight dose of insulin, there are no inexpensive methods for checking when and how much insulin is injected and transmitting the checked information.

To conventionally measure a dose of insulin, an amount of insulin in a syringe containing an injection liquid or a position of a syringe piston is measured. For an insulin pump similar to an insulin pen, the number of revolutions of a motor and a screw for moving a syringe piston is measured.

However, the above-mentioned techniques are difficult to apply to the structures of insulin pens that are available on the markets.

With a currently used insulin pen, a user determines a dose by turning a number sleeve of the insulin pen and, when the user presses a button disposed at the end of the insulin pen, a screw provided in the number sleeve is connected to a clutch and performs a spiral movement to move a piston forward within in an insulin injector. In other words, a screw nut is not moved during a rotary movement of the screw, and the screw moves forward while performing a spiral movement. When the screw performs only a rotary movement, it is easy to measure the number of revolutions corresponding to a spiral movement distance. However, when the screw directly moves forward while performing a spiral movement, it is difficult to measure the number of revolutions of the screw.

Moreover, when a dose is measured using a capacitance/inductance/optical mark, a measuring apparatus is disposed at the front of a syringe, which will increase a size thereof Also, manufacturing costs increase due to the addition of a physical quantity measuring apparatus to a disposable syringe.

SUMMARY OF THE INVENTION

An aspect of the present invention provides an apparatus and method for measuring a dose in an injector, which is capable of measuring a dose without modifying the mechanical structure of the injector.

In accordance with one aspect of the present invention, an apparatus for measuring a dose in an injector includes a number sleeve and an injector body. The number sleeve is provided to pass through an injector body and is connected to be spirally movable, and a pattern for dose measurement is formed on an outer periphery of the number sleeve. The injector body includes a sensor for sensing the pattern formed on the number sleeve when the number sleeve performs a spiral movement, and a controller for measuring a dose according to a spiral movement distance of the number sleeve through the sensor.

In accordance with another aspect of the present invention, there is provided a method for measuring a dose in an injector, wherein the injector includes a number sleeve passing through an injector body and having a pattern on an outer periphery thereof in a spiral direction, and the injector body having a sensor for sensing a change in the pattern formed on the number sleeve. The method includes sensing the change in the pattern formed on the number sleeve when the number sleeve performs a spiral movement while passing through the injector body, measuring a spiral movement distance of the number sleeve according to the change in the pattern, and measuring a dose according to the measured spiral movement distance.

BRIEF DESCRIPTION OF THE DRAWINGS

The above and other aspects, features and advantages of certain exemplary embodiments of the present invention will be more apparent from the following description taken in conjunction with the accompanying drawings, in which.

DETAILED DESCRIPTION OF EMBODIMENTS OF THE INVENTION

Embodiments of the present invention will be described in detail with reference to the accompanying drawings. In the following description, specific details such as detailed configuration and components are merely provided to assist the overall understanding of embodiments of the present invention. Therefore, it should be apparent to those skilled in the art that various changes and modifications of the embodiments described herein can be made without departing from the scope and spirit of the invention. Throughout the drawings, the same drawing reference numerals will be understood to refer to the same elements, features and structures. In addition, descriptions of well-known functions and constructions are omitted for the sake of clarity and conciseness.

Figure 1A:
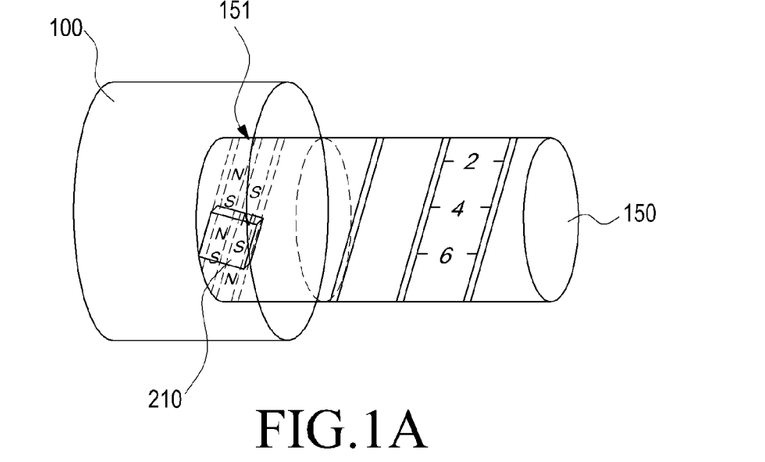
FIGS. 1A to 1C illustrate methods for measuring a dose in an injector according to the present invention.
Figure 1B:
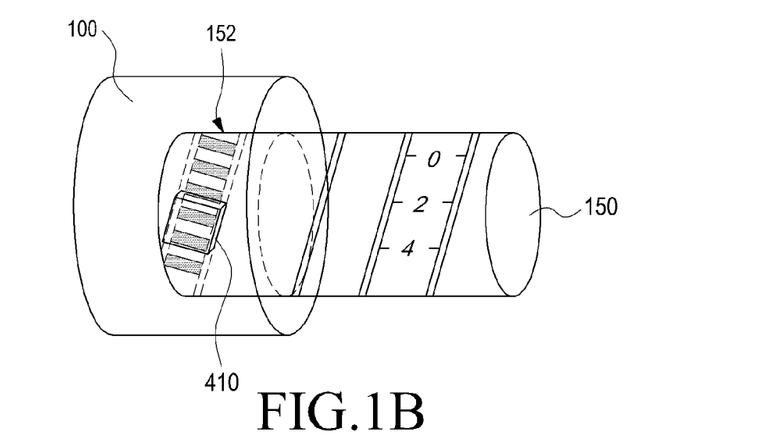
Figure 1C:
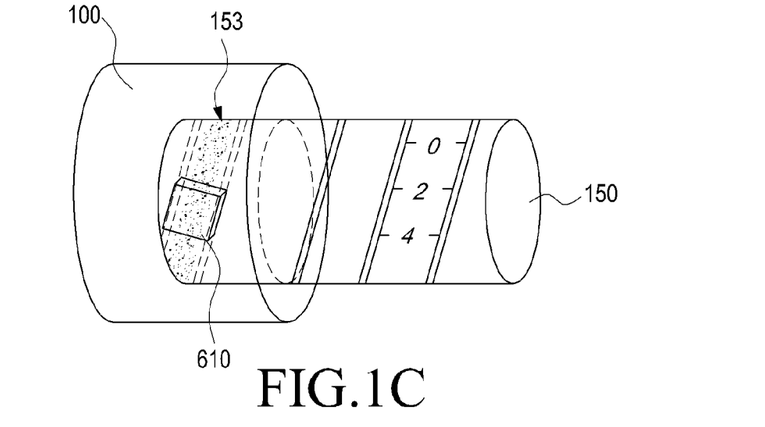

FIGS. 1A to 1C illustrate methods for measuring a dose in an injector according to the present invention.

Three methods for measuring a dose in an injector are illustrated in FIGS. 1A to 1C.

Referring to FIG. 1A, a dose is measured by sensing a change in a magnetic field. A number sleeve 150 is connected to an injector body 100 and is provided to pass through the injector body 100 and adjust a dose while performing a straight movement and a spiral movement, and a regular magnetic pattern 151 for measuring a dose is formed on the outer periphery of the number sleeve 150 in a spiral direction.

In addition, at least one sensor is provided on the inner periphery of the injector body 100 to sense a change in the magnetic pattern 151 of the number sleeve 150 when the number sleeve 150 performs a straight movement together with a spiral movement. A spiral movement distance of the number sleeve 150 is measured according to an output signal of the sensor, and a dose is measured according to the measured spiral movement distance.

Referring to FIG. 1B, a dose is measured by sensing a change in shading. A number sleeve 150 is provided to pass through an injector body 100 and adjust a dose while performing a straight movement and a spiral movement, and an optical pattern 152 for measuring a dose is formed on the outer periphery of the number sleeve 150 in a spiral direction. The optical pattern 152 has repeated shaded sections.

In addition, at least one optical encoder 410 is provided on the inner periphery of the injector body 100 to sense a change in the optical pattern 152 of the number sleeve 150 when the number sleeve 150 performs a straight movement together with a spiral movement. A spiral movement distance of the number sleeve 150 is measured according to a sense signal output from the optical encoder 410, and a dose is measured according to the measured spiral movement distance.

Referring to FIG. 1C, a dose is measured by sensing a movement distance of a surface image. A number sleeve 150 is provided to pass through an injector body 100 and adjust a dose while performing a straight movement and a spiral movement, and an image pattern 153 having uneven surface roughness is formed on the outer periphery of the number sleeve 150.

In addition, an optical tracker is provided on the inner periphery of the injector body 100 to sense the movement distance of the surface image pattern 153 having uneven surface roughness on the number sleeve 150 when the number sleeve 150 performs a straight movement together with a spiral movement. A spiral movement distance of the number sleeve 150 is measured by sensing the movement of the surface image through the optical tracker, and a dose is measured according to the measured spiral movement distance.

Figure 2A:
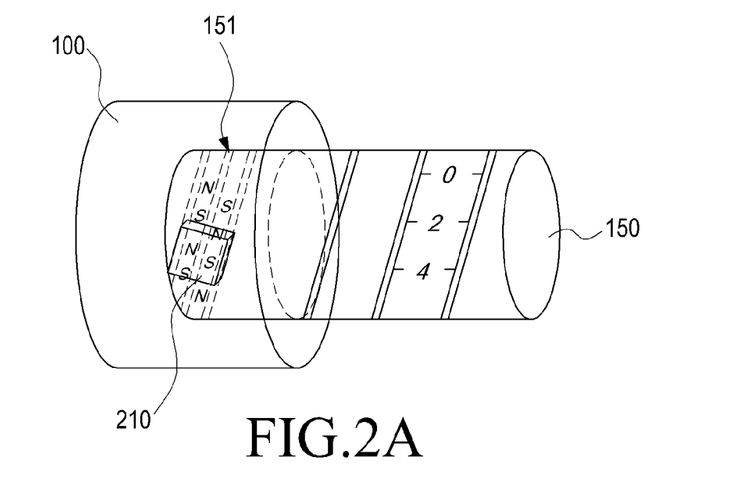
FIGS. 2A to 2C illustrate a method for measuring a dose in an injector according to a first embodiment of the present invention.
Figure 2B:
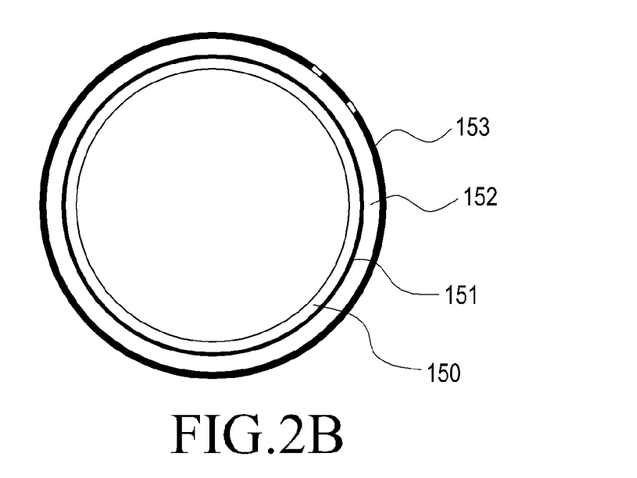
Figure 2C:
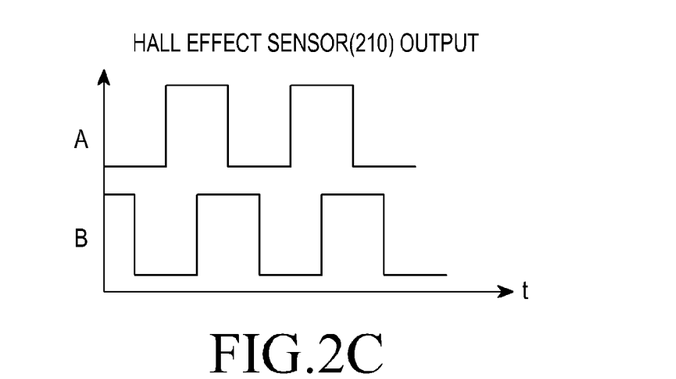
Figure 3:
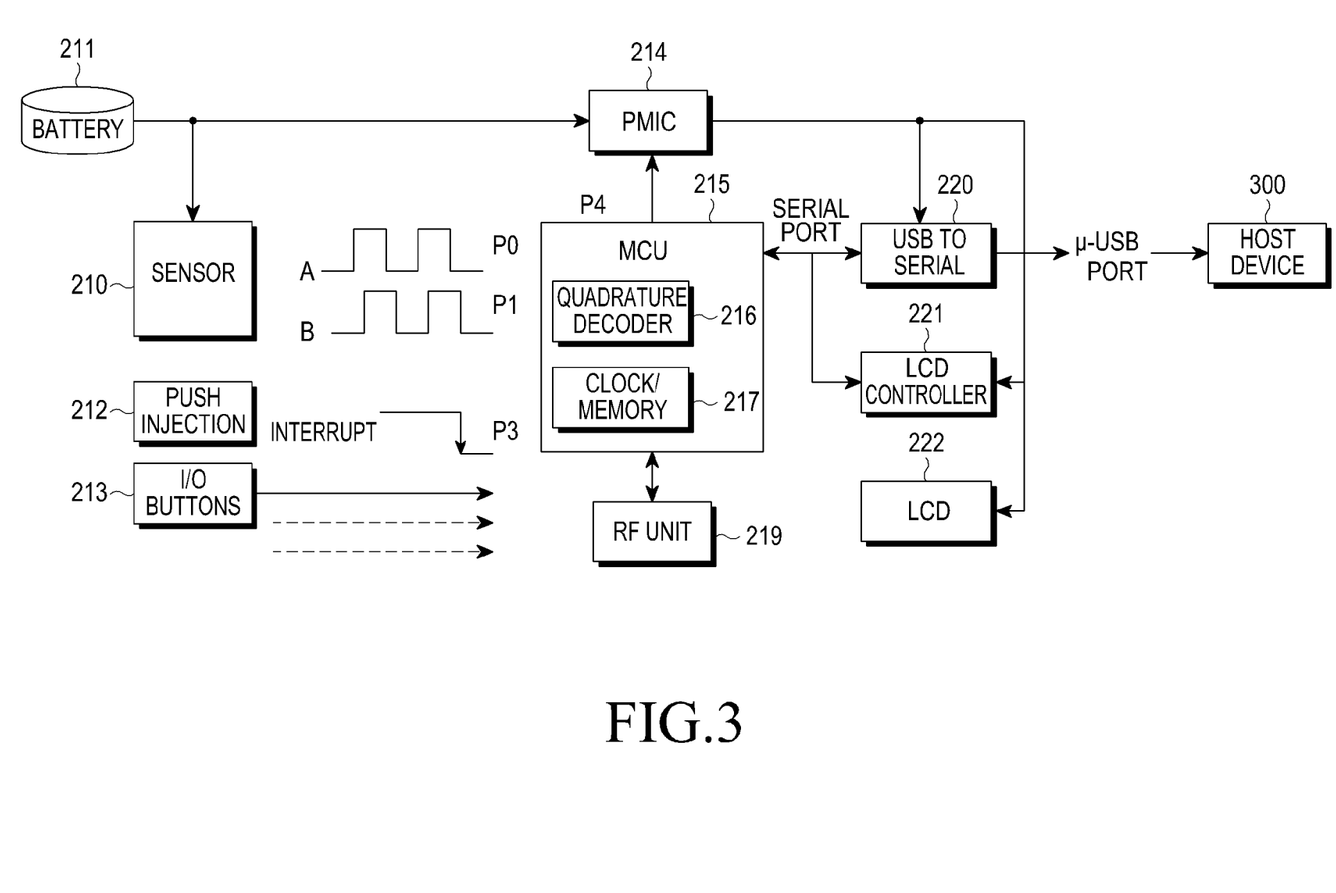
FIG. 3 illustrates the injector shown in FIG. 2A.

FIGS. 2A to 2C illustrate a method for measuring a dose in an injector according to a first embodiment of the present invention, and FIG. 3 is a block diagram of the injector shown in FIG. 2.

FIG. 2A illustrates a structure of an injector that may measure a dose by sensing a change in a magnetic field. A number sleeve 150 passes through an injector body 100 and moves straight while performing a spiral movement. A magnetic pattern 151 is wound around the outer periphery of the number sleeve 150 in a spiral direction, or a magnetized pattern is formed thereon in a spiral direction. The magnetic pattern 151 has N poles and S poles that may be formed regularly or continuously.

At least one sensor 210, also shown in FIG. 1A, is provided on the inner periphery of the injector body 100 in parallel with a spiral angle of the number sleeve 150, and the sensor 210 may be a Hall effect sensor or a magnetoresistive sensor.

When the number sleeve 150 performs a spiral movement while passing through the injection body 100, the sensor 210 senses the change in the magnetic field through the change in the magnetic pattern 151 and outputs the sense signal. A MicroController Unit (MCU) (hereinafter, a controller) 215 measures the spiral movement distance of the number sleeve 150 through the sense signal output from the sensor 210, and measures the dose according to the measured spiral movement distance.

FIG. 2B illustrates a cross section of the number sleeve 150 shown in FIG. 2A. Reference numerals 150 and 151 represent the number sleeve body and an adhesive, respectively. Reference numeral 152 represents the magnetic pattern 151 made of a rubber magnet or a flexible magnet having a thickness of 200 μm to 300 μm. Reference numeral 153 represents a polymer cover that is coated on the surface of the magnetic pattern 151 or can be coated thereon. Characters of the number sleeve 150 may be expressed on the polymer cover 153.

When two sensors A and B are provided, signals output when the change in the magnetic field is sensed through the change in the magnetic pattern are shown in FIG. 2C. A phase of the signal output from the sensor B lags behind a phase of the signal output from the sensor A by 90 degrees.

FIG. 3 illustrates the structure of the injector body 100 shown in FIG. 2A. A battery 211 supplies power to the components of the injector, and a Power Management Integrated Circuit (PMIC) 214 manages a power control.

At least one sensor 210 may be provided in the injector body. When the number sleeve 150 moves straight while performing the spiral movement, the sensor 210 senses the change in the magnetic field according to the change in the magnetic pattern 151 formed on the inner periphery of the number sleeve 150, and outputs signals shown in FIG. 2C.

The controller 215 may include a quadrature decoder 216 and a memory 217, both of which may be separately provided.

The quadrature decoder 216 divides a magnetic pattern pitch by four times. When N poles and S poles in the magnetic pattern of the number sleeve 150 are continuously magnetized, 2-mm pitch may be realized. Theoretically, the 0.5-mm spiral movement distance measurement can be achieved by the use of the quadrature decoder 216. Since 0.5-mm resolution makes it possible to divide 2 mm corresponding to 1 unit of the general number sleeve by four times, the dose measurement corresponding to the spiral movement distance may be more accurate.

The memory 217 stores the measured dose and the date and time of injection, and stores the dose corresponding to the spiral movement distance.

In addition, the controller 215 may extract from the memory 217 the dose corresponding to the spiral movement distance measured according to the change in the magnetic field, and display the extracted dose and the date and time of injection on a display 222 or transmit them to an external host device 300 automatically or by a user's selection.

A push injection button 212 is provided for starting the operation of the injector, and I/O buttons 213 are provided for displaying the dose and the date and time of injection, which are stored in the memory 217, on the display 222.

A Radio Frequency (RF) unit 219 may transmit the dose and the date and time of injection, which are stored in the memory 217, to an external device, such as a host device 300 of a medical center or hospital, by wireless under the control of the controller 215.

A Universal Serial Bus (USB) 220 is provided for a serial connection, and is connected to a USB port of the external host device 300 and may transmit the dose and the date and time of injection, which are stored in the memory 217, to the external device, such as the host device 300 of the medical center or hospital, by cable under the control of the controller 215.

A Liquid Crystal Display (LCD) controller 221 controls an LCD 222, which displays the measured dose and the date and time of injection under the control of the LCD controller 221.

The operation of measuring the dose in the injector shown in FIGS. 2A and 3 will be described below. If a user presses the push injection button 212 to start the operation of the injector, the number sleeve 150 performs a spiral movement and a straight movement while passing through the injector body 100. The sensor 210 of the injector body 100 senses the change in the magnetic field according to the change in the magnetic pattern 151 of the number sleeve 150, and outputs the sensed signal to the controller 215.

Using the sensed signal output from the sensor 210, the controller 215 measures the spiral movement distance of the number sleeve 150, extracts the dose corresponding to the measured spiral movement distance from the memory 217, and displays the extracted dose on the display 222 or transmits the extracted dose to the external host device 300.

The first embodiment of the present invention aims at adjusting the dose by measuring the dose using the magnetic pattern formed on the number sleeve 150 that performs the spiral movement and the straight movement. Therefore, if the number sleeve 150 moves straight while performing the spiral movement, the dose is measured and is simultaneously adjusted. Thereafter, if the user presses the button disposed at the end of the injector, the screw provided inside the number sleeve 150 is connected to the clutch. Accordingly, the number sleeve 150 moves the injector piston forward by the spiral movement, and the dose is thereby injected into the user.

Figure 4A:
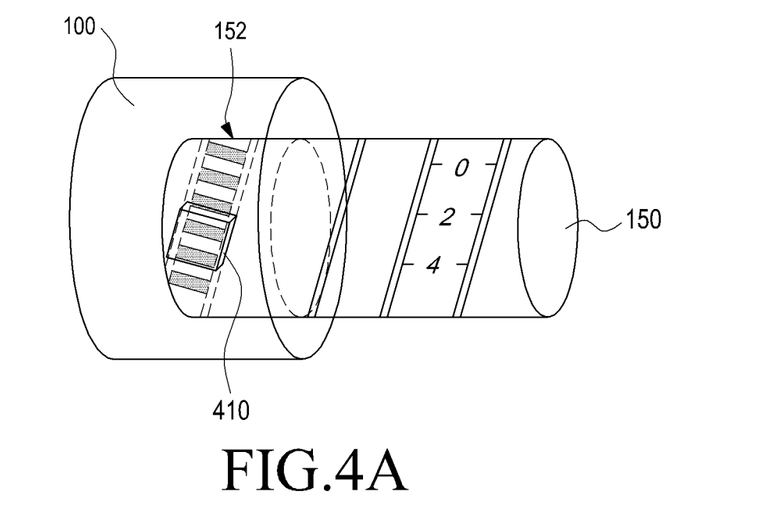
FIGS. 4A to 4C illustrate a method for measuring a dose in an injector according to a second embodiment of the present invention.
Figure 4B:
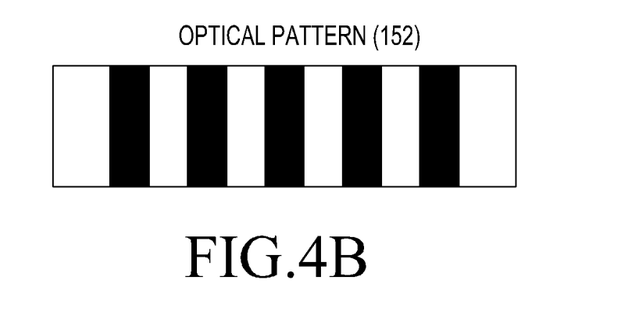
Figure 4C:
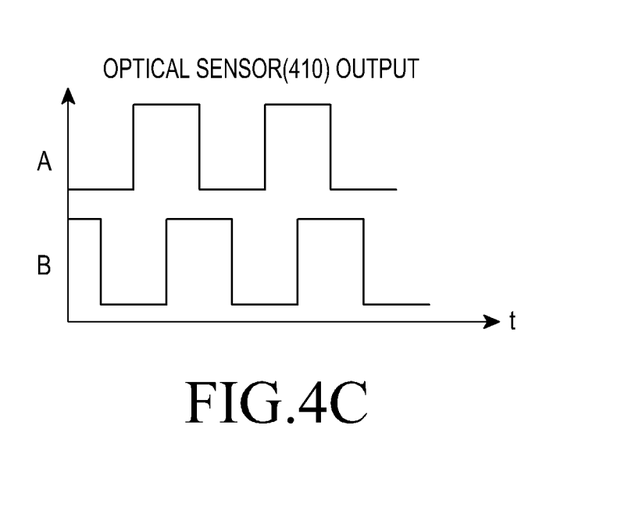
Figure 5:
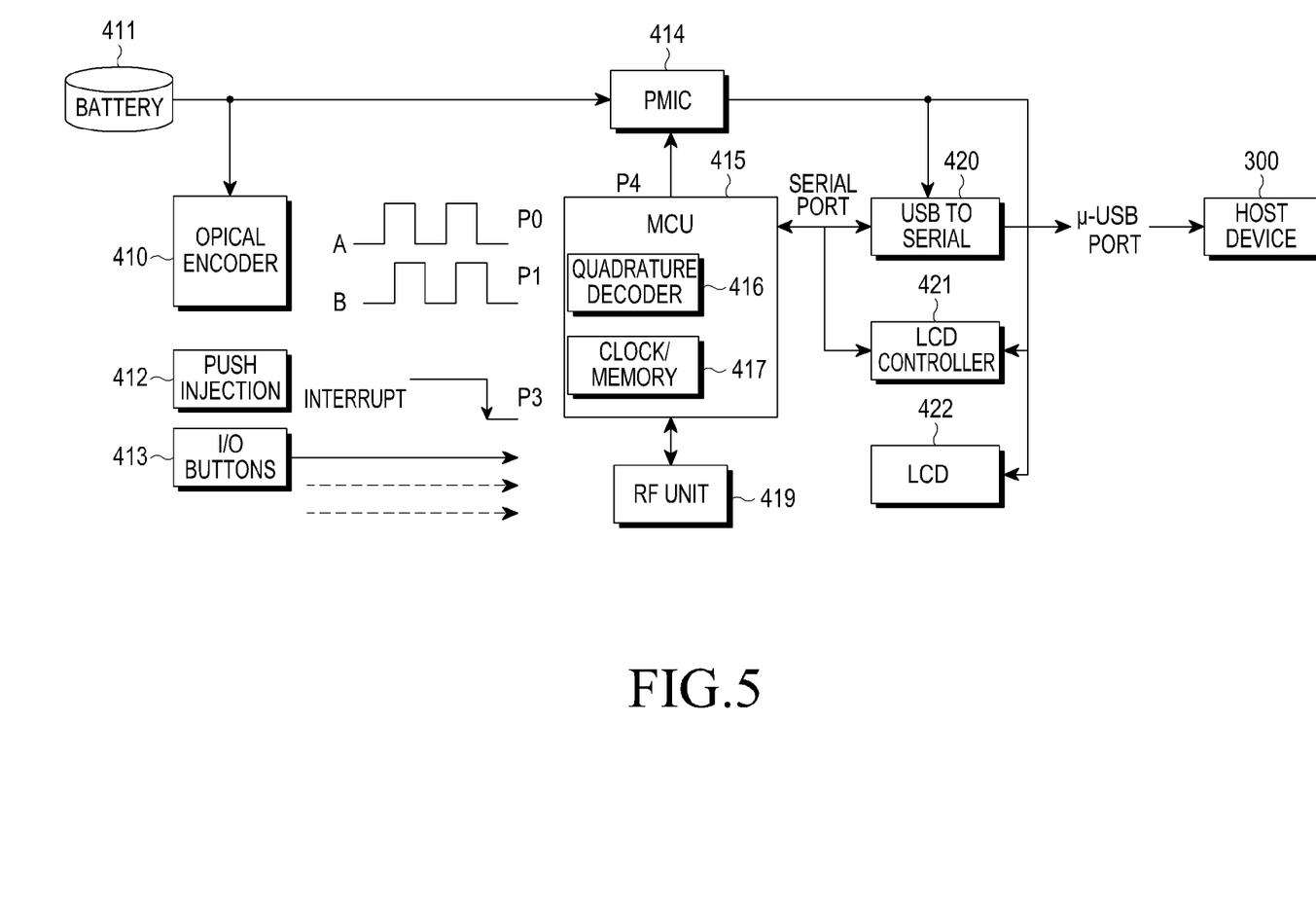
FIG. 5 illustrates the injector shown in FIG. 4A.

FIGS. 4A to 4C illustrate a method for measuring a dose in an injector according to a second embodiment of the present invention, and FIG. 5 is a block diagram of the injector shown in FIG. 4A.

FIG. 4A illustrates a structure of an injector that may measure a dose by sensing a change in shading. A number sleeve 150 passes through an injector body 100 and moves straight while performing a spiral movement. A reflective optical pattern 152 is formed on the outer periphery of the number sleeve 150 in a spiral direction. The reflective optical pattern 152 is formed by regular shading repetition.

FIG. 4B illustrates the optical pattern formed on the outer periphery of the number sleeve 150 by regular shading repetition.

At least one optical encoder 410, also shown in FIG. 4A, is provided on the inner periphery of the injector body 100 in parallel with a spiral angle of the number sleeve 150, and the optical encoder 410 includes a light emitting element and a light receiving element. Instead of the optical encoder, any type of sensors may be used as long as they can sense a change in shading. For example, a sensor having a combination of a photodiode (PD) and a light emitting diode (LED) may be used as the optical encoder 410.

When the number sleeve 150 performs a spiral movement while passing through the injection body 100, the optical encoder 410 senses the change in the shading through the change in the optical pattern 152 and outputs the sense signal. A microcontroller unit (MCU) (hereinafter, referred to as a controller) 415 measures a spiral movement distance of the number sleeve 150 through an output signal of the optical encoder 410, and measures a dose using the measured spiral movement distance.

When two optical encoders A and B are provided, signals output when the change in the shading is sensed through the change in the optical pattern are shown in FIG. 4C. A phase of the signal output from the optical encoder B lags behind a phase of the signal output from the optical encoder A by 90 degrees.

FIG. 5 illustrates the structure of the injector body 100 shown in FIG. 4A. A battery 411 supplies power to the components of the injector, and a PMIC 414 manages a power control.

At least one optical encoder 410 may be provided in the injector body 100, and the optical encoder 410 includes a light emitting element and a light receiving element. In addition, when the number sleeve 150 moves straight while performing the spiral movement, the optical encoder 410 senses the change in the magnetic field according to the change in the optical pattern formed on the inner periphery of the number sleeve 150, and outputs signals shown in FIG. 4C.

The controller 415 may include a quadrature decoder 416 and a memory 417, both of which may be separately provided.

The quadrature decoder 416 divides a magnetic pattern pitch by four times. When a 150 line-per-inch (lpi) reflective optical line pattern is used, 42-μm spiral movement distance measurement can be achieved through the quadrature decoder 416.

The memory 417 stores the measured dose and the date and time of injection, and stores the dose corresponding to the spiral movement distance.

In addition, the controller 415 may extract from the memory 417 the dose corresponding to the spiral movement distance measured according to the change in the shading, and display the extracted dose and the date and time of injection on a display 422 or transmit them to an external host device 300 automatically or by a user's selection.

A push injection button 412 is provided for starting the operation of the injector, and I/O buttons 413 are provided for displaying the dose and the date and time of injection, which are stored in the memory 417, on the display 422.

An RF unit 419 may wirelessly transmit the dose and the date and time of injection, which are stored in the memory 417, to the external device, such as the host device 300 of the medical center or hospital, under the control of the controller 415.

A USB 420 is provided for a serial connection, and is connected to a USB port of the external host device 300 and may transmit the dose and the date and time of injection, which are stored in the memory 417, to the external device, such as the host device 300 of the medical center or hospital, by cable under the control of the controller 415.

An LCD controller 421 controls an LCD 422, and the LCD 422 displays the measured dose and the date and time of injection under the control of the LCD controller 421.

The operation of measuring the dose in the injector shown in FIGS. 4A and 5 will be described below. If a user presses the push injection button 412 to start the operation of the injector, the number sleeve 150 performs a spiral movement and a straight movement while passing through the injector body 100. The optical encoder 410 of the injector body 100 senses the change in the shading according to the change in the optical pattern 152 of the number sleeve 150, and outputs a sense signal to the controller 415.

Using the sense signal output from the optical encoder 410, the controller 415 measures the spiral movement distance of the number sleeve 150, extracts the dose corresponding to the measured spiral movement distance from the memory 417, and displays the extracted dose on the display 422 or transmits the extracted dose to the external host device 300.

The second embodiment of the present invention aims at adjusting the dose by measuring the dose using the optical pattern 152 formed on the number sleeve 150 that performs the spiral movement and the straight movement. Therefore, if the number sleeve 150 moves straight while performing the spiral movement, the dose is measured and is simultaneously adjusted. Thereafter, if the user presses the button disposed at the end of the injector, a screw provided inside the number sleeve 150 is connected to a clutch. Accordingly, the number sleeve 150 moves the injector piston forward by the spiral movement, and the dose is thereby injected into the user.

Figure 6A:
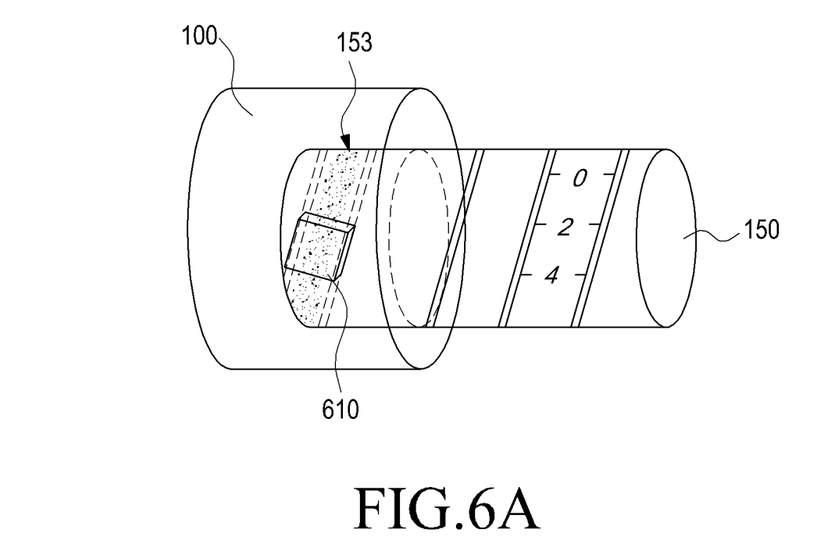
FIGS. 6A and 6B illustrate a method for measuring a dose in an injector according to a third embodiment of the present invention.
Figure 6B:
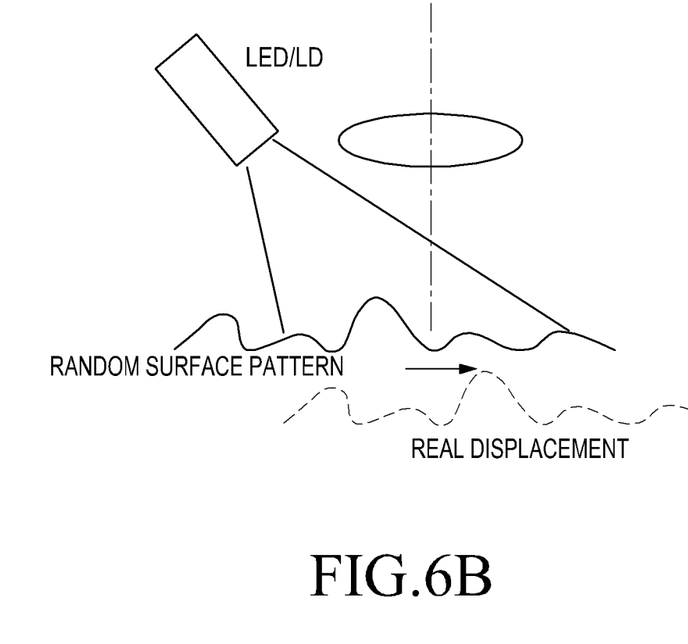
Figure 7:
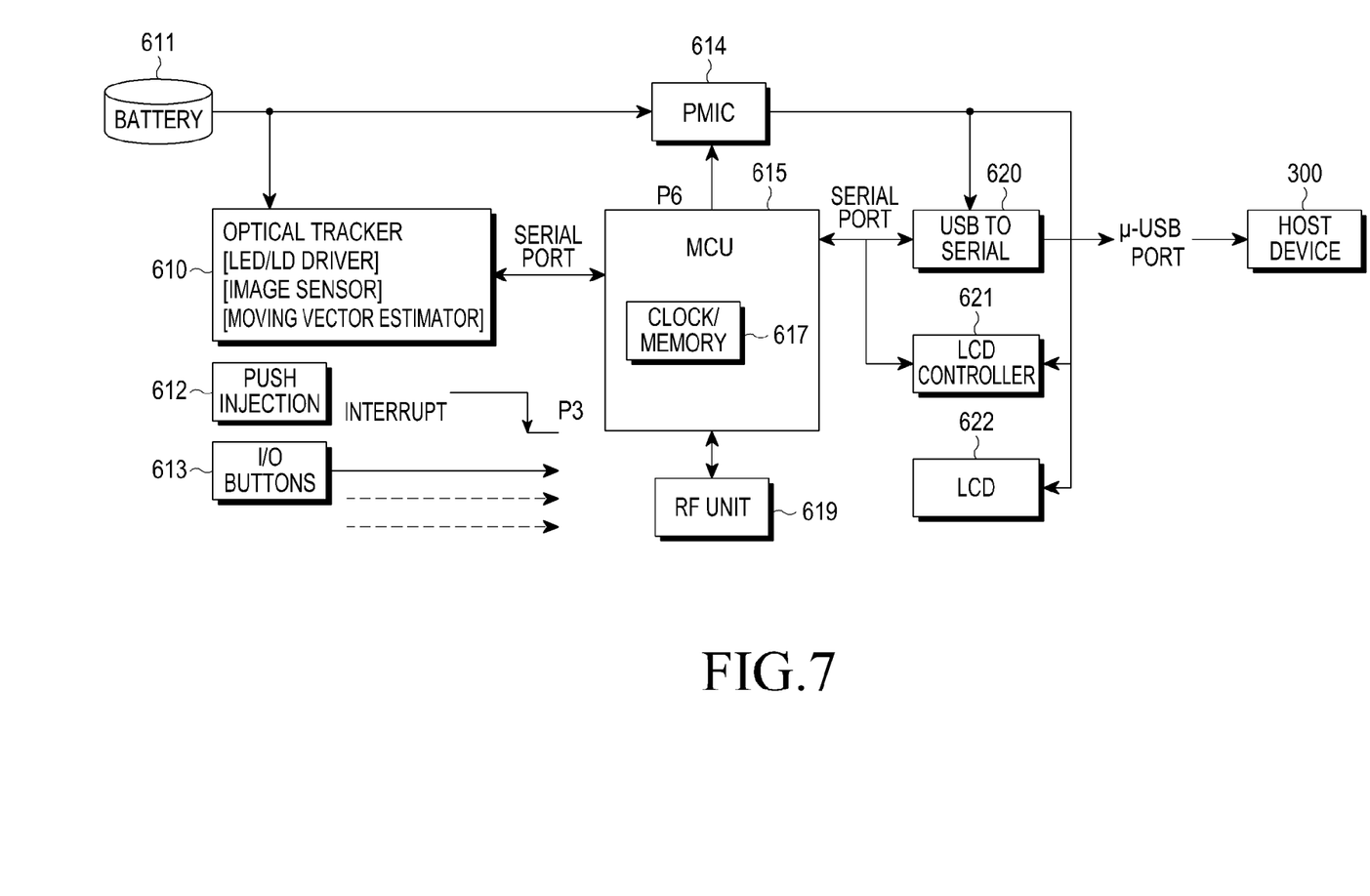
FIG. 7 illustrates the injector shown in FIG. 6A.
Figure 8:
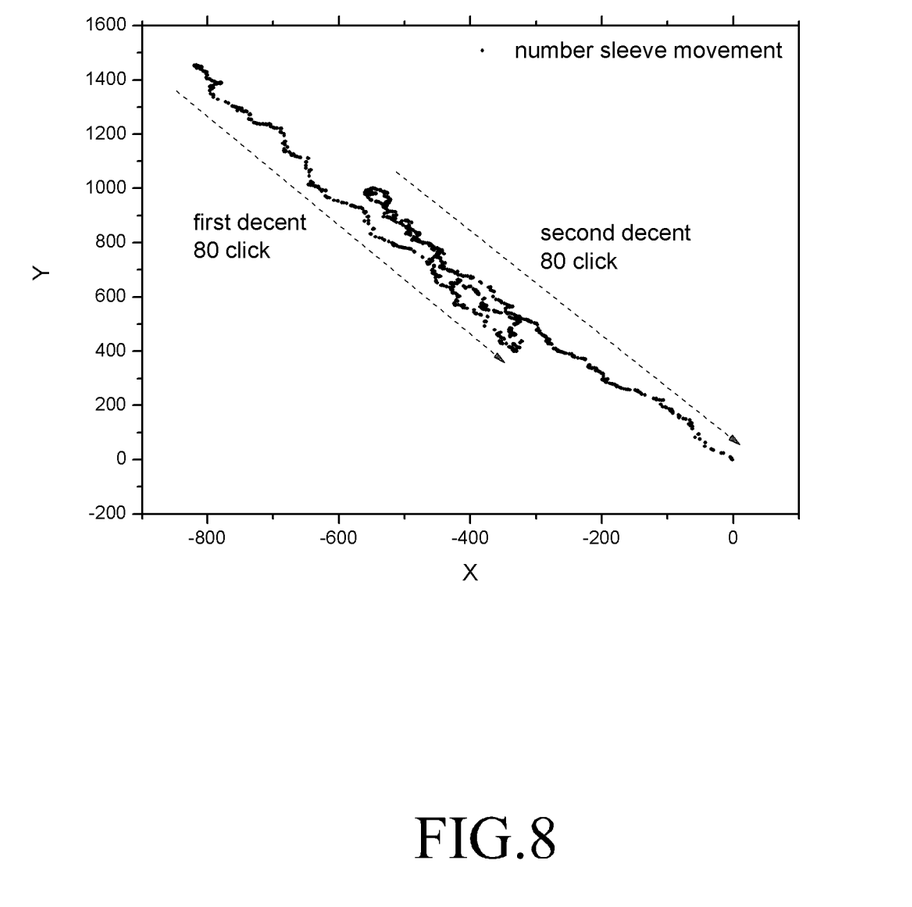
FIG. 8 illustrates results obtained by measuring a movement distance of a number sleeve shown in FIG. 6A.

FIGS. 6A and 6B illustrate a method for measuring a dose in an injector according to a third embodiment of the present invention, and FIG. 7 is a block diagram of the injector shown in FIG. 6A. FIG. 8 illustrates results obtained by measuring a movement distance of a number sleeve shown in FIG. 6A.

FIG. 6A illustrates a structure of an injector that may measure a dose through a movement detection of a surface image. A number sleeve 150 passes through an injector body 100 and moves straight while performing a spiral movement. An image pattern 153 having an uneven surface roughness is formed on the outer periphery of the number sleeve 150.

The surface roughness of the image pattern 153 has an irregular and random shape larger than 850 nm, which is used as a light source of an optical system, so as to obtain the formed image through the optical system.

An optical tracker 610 is provided on the inner periphery of the injector body 100 in parallel with a spiral angle of the number sleeve 150.

When the number sleeve 150 performs a spiral movement while passing through the injection body 100, the optical tracker 610 forms the surface image, senses the movement of the surface image through the change in the pattern of the formed surface image, and outputs the sensed movement to a microcontroller unit (MCU) (hereinafter, controller) 615 of the injector body 100, which measures a spiral movement distance of the number sleeve 150 through an algorithm, and measures a dose according to the measured spiral movement distance.

FIG. 6B illustrates the operation of forming the surface image using the light source Light Emitting Diode (LED/LD) of the optical tracker 610 and sensing the formed surface image using an image sensor of the optical tracker 610.

FIG. 7 illustrates the structure of the injector body 100 shown in FIG. 6A. A battery 611 supplies power to the components of the injector, and a PMIC 614 manages a power control.

The optical tracker 610 includes a light source LED/LD, an image sensor, and a moving vector estimator. When the number sleeve 150 performs a spiral movement while passing through the injector body 100, the light source forms the surface image as shown in FIG. 6B, and the image sensor senses the formed surface image. The moving vector estimator senses the movement distance of the surface image through the change in the pattern of the formed surface image, and outputs the sensed movement distance to the controller 615.

Instead of the optical tracker 610, an optical joystick or an optical mouse module may be used to measure the movement distance of the surface image.

The controller 615 may include a memory 617, which may be separately provided.

The memory 617 stores the measured dose, the date and time of injection, and the dose corresponding to the spiral movement distance, and stores an algorithm for measuring the spiral movement distance of the number sleeve 150 according to the movement distance of the surface image.

The controller 615 may measure a 36-μm spiral movement distance through a 1:1 image system.

When the movement distance of the surface image is outputted from the optical tracker 610, the controller 615 measures the spiral movement distance of the number sleeve 150 corresponding to the movement distance of the surface image through the algorithm stored in the memory 617, and measures the dose according to the measured spiral movement distance.

Moreover, the controller 615 may extract from the memory 617 the dose corresponding to the spiral movement distance measured according to the movement distance of the surface image, and display the extracted dose and the date and time of injection on a display 622 or transmit them to the external host device 300 automatically or by a user's selection.

A push injection button 612 is provided for starting the operation of the injector, and I/O buttons 613 are provided for displaying the dose and the date and time of injection, which are stored in the memory 617, on the display 622.

An RF unit 619 may wirelessly transmit the dose and the date and time of injection, which are stored in the memory 617, to an external device, such as a host device 300 of a medical center or hospital, under the control of the controller 615.

A USB 620 is provided for a serial connection, and is connected to a USB port of the external host device 300 and may transmit the dose and the date and time of injection, which are stored in the memory 617, to the external device, such as the host device 300 of the medical center or hospital, by cable under the control of the controller 615.

An LCD controller 621 controls an LCD 622, which displays the measured dose and the date and time of injection under the control of the LCD controller 621.

The operation of measuring the dose in the injector shown in FIGS. 6A and 7 will be described below. If a user presses the push injection button 612 to start the operation of the injector, the number sleeve 150 performs a spiral movement and a straight movement while passing through the injector body 100. The optical tracker 610 of the injector body 100 senses the movement distance of the surface image through the change in the image pattern 153 of the number sleeve 150, and outputs the sensed movement distance to the controller 615.

Using the movement distance of the surface image, which is output from the optical tracker 610, the controller 615 measures the spiral movement distance of the number sleeve 150, extracts the dose corresponding to the measured spiral movement distance from the memory 617, and displays the extracted dose on the display 622 or transmits the extracted dose to the external host device 300.

The third embodiment of the present invention aims at adjusting the dose by measuring the dose using the optical pattern formed on the number sleeve 150 that performs the spiral movement and the straight movement. Therefore, if the number sleeve 150 moves straight while performing the spiral movement, the dose is measured and is simultaneously adjusted. Thereafter, if the user presses the button disposed at the end of the injector, a screw provided inside the number sleeve 150 is connected to a clutch. Accordingly, the number sleeve 150 moves an injector piston forward by the spiral movement, and the dose is thereby injected into the user.

FIG. 8 illustrates results obtained by measuring the movement distance of the surface image according to the spiral movement and the straight movement of the number sleeve shown in FIG. 6A.

As is apparent from the foregoing description, according to embodiments of the present invention, provided is an apparatus and method for conveniently measuring the dose in the injector. Since the number sleeve of the injector, the stability and reliability of which have already been verified, is used for adjusting the dose without modifying the mechanical structure thereof, the limit of the dose measurement may be overcome and the mass production and production cost reduction may be achieved.

While the invention has been shown and described with reference to embodiments thereof, it will be understood by those skilled in the art that various changes in form and details may be made therein without departing from the spirit and scope of the invention as defined by the appended claims and their equivalents.

What is claimed is:

1. An apparatus for measuring a dose in an injector, comprising:
a number sleeve that passes through an injector body and is connected to the injector body to be spirally movable, a pattern for dose measurement being formed on an outer periphery of the number sleeve; and
the injector body comprising:
a sensor for sensing a change in the pattern formed on the number sleeve when the number sleeve performs a spiral movement; and
a controller for measuring a dose according to a spiral movement distance of the number sleeve through the change in the pattern formed on the number sleeve sensed by the sensor.

2. The apparatus of claim 1, wherein the controller displays the measured dose and date and time of injection, and transmits the measured dose and the date and time of injection to an external device.

3. The apparatus of claim 1, wherein the injector body further comprises:
a display for displaying a measured dose, date and time of injection; and
a Radio Frequency (RF) unit for transmitting the measured dose, date and time of injection.

4. The apparatus of claim 1, wherein, when a magnetic pattern having N pole and S pole is formed on the number sleeve in a spiral direction, the sensor of the injector body comprises at least one sensor that is disposed in parallel with a spiral angle of the number sleeve and senses a change in a magnetic field through a change in the magnetic pattern.

5. The apparatus of claim 4, wherein the sensor is a Hall effect sensor or a magnetoresistive sensor.

6. The apparatus of claim 1, wherein, when an optical pattern having shaded sections is formed on the number sleeve in a spiral direction, the sensor of the injector body comprises at least one optical encoder that is disposed in parallel with a spiral angle of the number sleeve and senses a change in the shaded sections through a change in the optical pattern.

7. The apparatus of claim 6, wherein the optical encoder comprises a light emitting element and a light receiving element.

8. The apparatus of claim 1, wherein, when an image pattern having uneven surface roughness is formed on the number sleeve in a spiral direction, the sensor of the injector body comprises an optical tracker that is disposed in parallel with a spiral angle of the number sleeve and senses a movement distance of a surface image through a change in the image pattern.

9. The apparatus of claim 8, wherein the optical tracker comprises:
a light source for forming the surface image;
an image sensor for sensing the formed surface image; and
a moving vector estimator for sensing the movement distance of the surface image through a change in a pattern of the formed surface image.

10. A method for measuring a dose in an injector, the injector including a number sleeve passing through an injector body and having a pattern on an outer periphery thereof in a spiral direction, and the injector body having a sensor for sensing a change in the pattern formed on the number sleeve, the method comprising:
sensing the change in the pattern formed on the number sleeve when the number sleeve performs a spiral movement while passing through the injector body;
measuring a spiral movement distance of the number sleeve according to the change in the pattern; and
measuring a dose according to the measured spiral movement distance.

11. The method of claim 10, further comprising:
displaying the measured dose, date and time of injection; and
transmitting the measured dose, date and time of injection to an external device.

12. The method of claim 10, wherein, when a magnetic pattern having N pole and S pole is formed on the number sleeve in a spiral direction and the sensor of the injector body is at least one sensor disposed in parallel with a spiral angle thereof, the sensing of the change in the pattern comprises sensing a change in a magnetic field through a change in the magnetic pattern according to the spiral movement of the number sleeve.

13. The method of claim 12, wherein the sensor is a Hall effect sensor or a magnetoresistive sensor.

14. The method of claim 10, wherein, when an optical pattern having shaded sections is formed on the number sleeve in a spiral direction and the sensor of the injector body is at least one optical encoder disposed in parallel with a spiral angle thereof, the sensing of the change in the pattern comprises sensing a change in the shaded sections through a change in the optical pattern according to the spiral movement of the number sleeve.

15. The method of claim 14, wherein the optical encoder comprises a light emitting element and a light receiving element.

16. The method of claim 10, wherein, when an image pattern having uneven surface roughness is formed on the number sleeve in a spiral direction and the sensor of the injector body is an optical tracker disposed in parallel with a spiral angle, the sensing of the change in the pattern comprises sensing a movement distance of a surface image through a change in the image pattern according to the spiral movement of the number sleeve.

17. The method of claim 16, wherein the sensing of the movement distance of the surface image comprises:
- forming the surface image through a light source;
- sensing the formed surface image; and
- sensing the movement distance of the surface image through the change in the pattern of the formed surface image.

* * * * *